US009745236B2

United States Patent
Frey et al.

(10) Patent No.: US 9,745,236 B2
(45) Date of Patent: Aug. 29, 2017

(54) METHOD FOR RECOVERING DI-TRIMETHYLOLPROPANE BY DISTILLATION

(71) Applicant: Oxea GmbH, Oberhausen (DE)

(72) Inventors: Guido D. Frey, Riedstadt (DE); Norman Nowotny, Essen (DE); Kurt Schalapski, Oberhausen (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 659 days.

(21) Appl. No.: 14/351,306

(22) PCT Filed: Oct. 24, 2012

(86) PCT No.: PCT/EP2012/004439
§ 371 (c)(1),
(2) Date: Apr. 11, 2014

(87) PCT Pub. No.: WO2013/072007
PCT Pub. Date: May 23, 2013

(65) Prior Publication Data
US 2014/0284202 A1    Sep. 25, 2014

(30) Foreign Application Priority Data
Nov. 19, 2011   (DE) .................. 10 2011 118 953 U (51) Int. Cl.
*B01D 1/06*     (2006.01)
*B01D 3/14*     (2006.01)
(Continued)

(52) U.S. Cl.
CPC .............. *C07C 29/80* (2013.01); *C07C 41/42* (2013.01); *C07C 41/44* (2013.01); *B01D 1/06* (2013.01);
(Continued)

(58) Field of Classification Search
CPC ....... C07C 43/13; C07C 43/132; C07C 41/42; C07C 29/80; B01D 2253/206;
(Continued)

(56) References Cited

U.S. PATENT DOCUMENTS

| 3,097,245 | A | * | 7/1963 | Russell | .................. | C08G 63/12 568/601 |
| 3,740,322 | A | | 6/1973 | Wada et al. | | |

(Continued)

FOREIGN PATENT DOCUMENTS

| DE | 2058518 | | 6/1971 |
| DE | 2358297 | A1 | 5/1974 |

(Continued)

OTHER PUBLICATIONS

International Search Report dated Jan. 22, 2013.

*Primary Examiner* — In Suk Bullock
*Assistant Examiner* — Jonathan Pilcher
(74) *Attorney, Agent, or Firm* — Michael W Ferrell (57) ABSTRACT

Distillative process for obtaining ditrimethylolpropane from solutions includes separating ditrimethylolpropane from the solution in a first distillation unit into a first tops fraction comprising low-boiling compounds having a lower boiling point than ditrimethylolpropane and a first bottoms fraction; introducing the first bottoms fraction into a second distillation unit having at least 5 theoretical plates, said unit being configured as a thin-film evaporator with a column attachment and drawing off a second tops fraction comprising intermediate-boiling compounds having a lower boiling point than ditrimethylolpropane as well as withdrawing a second bottoms fraction from the second distillation unit and introducing the second bottoms fraction into a third distillation unit having at least 4 theoretical plates, said unit being configured as a thin-film evaporator with a column attachment, such that ditrimethylolpropane is obtained as a third (Continued)

tops fraction and high boilers are removed as a third bottoms fraction.

20 Claims, 1 Drawing Sheet

(51) Int. Cl.
  *C07C 29/80* (2006.01)
  *C07C 41/42* (2006.01)
  *C07C 41/44* (2006.01)
  *C07C 43/13* (2006.01)
(52) U.S. Cl.
  CPC ............... *B01D 1/065* (2013.01); *B01D 3/14* (2013.01); *B01D 3/143* (2013.01); *B01D 3/148* (2013.01); *C07C 43/13* (2013.01); *C07C 43/132* (2013.01)
(58) Field of Classification Search
  CPC .......... B01D 3/143; B01D 3/148; B01D 3/10; B01D 3/101; B01D 3/103; B01D 3/105; B01D 3/106; B01D 3/108; B01D 3/12; B01D 3/14; B01D 1/06; B01D 1/065; B01D 1/08; B01D 1/10; B01D 1/12
  See application file for complete search history.

(56) References Cited

U.S. PATENT DOCUMENTS

| 3,962,347 | A | 6/1976 | Herz |
| 5,149,861 | A | 9/1992 | Merger et al. |
| 5,948,943 | A | 9/1999 | Supplee et al. |
| 6,265,623 | B1 | 7/2001 | Morawietz et al. |
| 6,692,616 | B2 | 2/2004 | Dernbach et al. |
| 7,241,914 | B2 * | 7/2007 | Wartini ............ C07C 29/80 560/198 |
| 8,642,816 | B2 | 2/2014 | Rauchschwalbe et al. |
| 2002/0033325 | A1 * | 3/2002 | Ninomiya ............ C07C 41/01 203/48 |
| 2004/0254405 | A1 | 12/2004 | Kuzuhara et al. |
| 2005/0010065 | A1 * | 1/2005 | Wartini ............ C07C 51/50 560/224 |
| 2005/0148802 | A1 * | 7/2005 | Wartini ............ C08G 65/2609 568/591 |
| 2005/0203268 | A1 * | 9/2005 | Wartini ............ C07C 29/80 528/272 |
| 2013/0131391 | A1 | 5/2013 | Kreickmann et al. |

FOREIGN PATENT DOCUMENTS

| DE | 3715035 | A1 | 11/1988 |
| DE | 19840276 | A1 | 3/2000 |
| DE | 19963435 | A1 | 7/2001 |
| DE | 10058303 | 1 | 5/2002 |
| DE | 102008038021 | A1 | 2/2010 |
| DE | 102010033844 | A1 | 2/2012 |
| EP | 1178030 | A2 | 2/2002 |
| EP | 2204356 | A1 | 7/2010 |
| WO | 9205134 | A1 | 4/1992 |
| WO | 9717313 | A1 | 11/1996 |
| WO | 9701523 | | 1/1997 |
| WO | 9828253 | A1 | 7/1998 |
| WO | 2004013074 | A1 | 7/2003 |

* cited by examiner

METHOD FOR RECOVERING DI-TRIMETHYLOLPROPANE BY DISTILLATION

CLAIM FOR PRIORITY

This application is a national phase application of PCT/EP2012/004439 FILED Oct. 24, 2012 which was based on application DE 10 2011 118 953.3 FILED Nov. 19, 2011. The priorities of PCT/EP2012/004439 and DE 10 2011 118 953.3 are hereby claimed and their disclosures incorporated herein by reference.

TECHNICAL FIELD

The present invention relates to a distillative process for obtaining ditrimethylolpropane.

BACKGROUND

Trimethylolpropane is a trihydric alcohol which is of significance for the production of coating materials, polyurethanes and polyesters, for example of alkyd resins. Trimethylolpropane is produced industrially by condensation reaction of n-butyraldehyde with formaldehyde according to different variants.

In what is called the hydrogenation process, at least two moles of formaldehyde are added onto one mole of n-butyraldehyde in the presence of a catalytic amount of a tertiary amine via the monomethylolbutyraldehyde intermediate to initially give dimethylolbutyraldehyde, which is then converted to trimethylolpropane in a hydrogenation step. According to the process described in WO98/28253 A1, formaldehyde is used with an up to eight-fold molar excess. The reaction mixture obtained from the aldol addition step is worked up either by distillation or by phase separation. In the distillative workup, unconverted or partly converted starting compounds are drawn off as volatile components and recycled into the reaction stage, while the bottom product is converted further. If, instead of the distillative workup, the reaction mixture is separated in a phase separator into the aqueous and organic phases, the organic phase is returned to the aldol addition and the aqueous phase is processed further. There follows a catalytic and/or thermal treatment in order to convert monomethylolbutyraldehyde to dimethylolbutyraldehyde. By-products formed are removed by distillation and the bottom product of this distillation is subsequently catalytically hydrogenated to obtain trimethylolpropane. The crude trimethyl-propane obtained is subsequently subjected to a purifying distillation. After removal of low and medium boilers, purified trimethylolpropane is obtained as an intermediate fraction, while higher-boiling condensation products within which trimethylolpropane equivalents are bound are obtained as the tailings or bottoms fraction.

In addition to the hydrogenation process, trimethylolpropane is also prepared industrially by what is known as the Cannizzaro reaction. In a first reaction stage, n-butyraldehyde and formaldehyde are reacted with addition of stoichiometric amounts of a base to give dimethylolbutyraldehyde, which is subsequently reduced with excess formaldehyde to give trimethylolpropane, while one equivalent of formate is formed simultaneously. Typically, the base used is an aqueous solution of an alkali metal or alkaline earth metal compound, for example sodium hydroxide, potassium hydroxide or calcium hydroxide. Since one equivalent of alkali metal or alkaline earth metal formate is obtained as a coproduct in the Cannizzaro process, the economic viability of this process variant also depends on the marketing opportunities for this coproduct. The workup of the aqueous reaction solution obtained, which comprises trimethylolpropane, alkali metal or alkaline earth metal formate and excess base, is effected generally by extraction. After neutralization of the excess base, the aqueous solution is extracted with an organic solvent, for example with ethyl acetate. The organic phase is separated from the aqueous phase, which comprises the alkali metal or alkaline earth metal formates in dissolved form, and, after removal of the extractant, trimethylolpropane is obtained by distillation. The resulting trimethylolpropane can be subjected to further purification processes. According to U.S. Pat. No. 5,603,835, an aqueous solution is first prepared from resulting trimethylolpropane, and is extracted once again with an organic solvent, for example with methyl tert-butyl ether. Trimethylolpropane is obtained from the resulting aqueous solution with an improved colour number of less than 100 APHA units.

According to the process known from U.S. Pat. No. 5,948,943, the aqueous, crude reaction solution obtained after the Cannizzaro reaction is treated with a suitable organic solvent at such a temperature that only one liquid phase leaves the extraction vessel. In the subsequent cooling outside the extraction vessel, the aqueous phase separates from the organic phase, and trimethylolpropane can be isolated from the aqueous phase with a colour number of less than 100 APHA.

It is likewise known that the Cannizzaro reaction can be performed with an organic base, for example with a tertiary amine. According to the procedure known from WO97/17313 A1, formaldehyde is reacted with n-butyraldehyde in the presence of stoichiometric amounts of a tertiary amine, forming one equivalent of ammonium formate. Subsequently, water, excess tertiary amine and excess formaldehyde are removed from the crude mixture, and the remaining mixture is heated. This dissociates the ammonium formate to the tertiary amine and formic acid, and the tertiary amine and further volatile constituents are removed, resulting in the formation of trimethylolpropane formate. The tertiary amine removed is either recycled into the Cannizzaro stage or used as a catalyst for the transesterification of the trimethylolpropane formate in a downstream reaction with an added lower aliphatic alcohol. The trimethylolpropane released is subsequently isolated from the crude product.

Irrespective of whether the preparation of trimethylolpropane is effected by the hydrogenation process using catalytic amounts of a tertiary amine, by the Cannizzaro process with molar amounts of a tertiary amine and subsequent transesterification of the trimethylolpropane formate formed, or by the Cannizzaro process with molar amounts of alkali metal or alkaline earth metal hydroxides and the extractive removal thereof, the crude trimethylolpropane obtained is subjected to a single or multiple distillative purification, which is effected under reduced pressure due to the high boiling point. According to DE 100 58 303 A1, the distillative workup of the trimethylolpropane is combined with an ion exchanger treatment, in which case either the aldolization output or the hydrogenation output is contacted with a strongly basic ion exchanger before the distillative workup.

Distillative purification gives rise to high-boiling fractions with a higher boiling point compared to trimethylolpropane, or residues in which derivatives of trimethylolpropane are present and have formed therefrom by reaction with, for example, methanol, formaldehyde or else with a further molecule of trimethylolpropane in the upstream reactions. Among these derivatives, particularly formaldehyde-containing acetals are represented, which are characterized by the structural element —O—CH$_2$—O— and can also be regarded as formals. Among the formals, the following linear and cyclic formals of trimethylolpropane can be described structurally:

Monocyclic formal of trimethylolpropane:

Formula I

Linear bistrimethylolpropane formal:

[C$_2$H$_5$C(CH$_2$OH)$_2$CH$_2$O]$_2$CH$_2$     Formula II

Methyl (monolinear) formal of trimethylolpropane:

C$_2$H$_5$C(CH$_2$OH)$_2$CH$_2$OCH$_2$OCH$_3$     Formula III

Methyl (bislinear) formal of trimethylolpropane:

C$_2$H$_5$C(CH$_2$OH)$_2$CH$_2$OCH$_2$OCH$_2$OCH$_3$     Formula IV

In this context, the monocyclic formal of trimethylolpropane (I) boils at a lower temperature than trimethylolpropane itself. The methanol-derived formals (III) and (IV) have a boiling point comparable to trimethylolpropane, while the linear bistrimethylol-propane formal (formula II) is present as a high-boiling component. In addition, further linear and cyclic oxygen compounds, such as the cyclic formal of ditrimethylolpropane Formula V are present in the distillation residues.

Likewise present in the high-boiling fractions and residues of the distillative workup of crude trimethylolpropane are also substantial amounts of ditrimethylolpropane [C$_2$H$_5$C(CH$_2$OH)$_2$—CH$_2$—]$_2$—O and trimethylolpropane itself. Additionally present in small amounts are low-boiling components, such as methanol, 2-methylbutanol or 2-ethyl-2-methyl-1,3-propanediol.

Since the high-boiling fractions and residues of the distillative workup of trimethylolpropane include considerable amounts of derivatives in which equivalents of trimethylolpropane are chemically bound, a number of processes are proposed to dissociate especially formaldehyde-containing acetals and to release trimethylolpropane, in order in this way to improve the yield of the overall trimethylolpropane preparation process. According to WO 2004/013074 A1, the high-boiling fractions and distillation residues obtained in the trimethylolpropane preparation are treated with acid, and the water content in the reaction mixture should be 20-90% by weight. It is possible either to obtain trimethylolpropane by distillation from the acid-treated product or to recycle the treated product into the hydrogenation stage of dimethylolbutyraldehyde to give trimethylol-propane.

The hydrogenating dissociation of linear or cyclic acetals in aqueous solutions in the presence of a heterogeneous hydrogenation catalyst to give the desired polyhydric alcohol is known from DE 198 40 276 A1. The process requires hydrogenation temperatures above 160° C. in order to suppress the harmful influence of formates, which may still be present particularly in the case of working by the Cannizzaro process, on the hydrogenation performance of the catalyst. The hydrogenating, catalytic dissociation can likewise be performed in the presence of an acid, for example in the presence of a lower carboxylic acid or acidic solids. According to WO 97/01523, the hydrogenation temperature can be lowered, but a high weight ratio of the catalytically active metal to the cyclic formal then has to be established in order to achieve an acceptable splitting rate.

The high-boiling fractions and the residues of the distillative workup of the trimethylolpropane preparation comprise, in addition to the aforementioned formaldehyde-containing acetals, also significant amounts of ditrimethylolpropane, which is likewise of industrial significance as a valuable starting material for production of alkyd resins, plasticizers and lubricants. The prior art discloses processes for obtaining ditrimethylolpropane from these residues, and further purifying product thus obtained if required.

According to DE 2058518 A1, the ditrimethylolpropane-containing distillation residue is subjected to a steam distillation with superheated steam under reduced pressure. After removal of water, ditrimethylolpropane is obtained from the resulting aqueous distillate, and can be recrystallized if required from an organic solvent, for example acetone.

The prior art makes several references to difficulties associated with the distillative purification of ditrimethylolpropane from the secondary streams of trimethylolpropane preparation. Firstly, the ditrimethylolpropane content in the distillation residue can vary considerably. In addition, the distillation residue likewise comprises high-boiling linear bistrimethylolpropane formal (formula II), which can be removed only with very great difficulty. The high boiling point of ditrimethylolpropane also requires the use of very low distillation pressures and high distillation temperatures, and so decomposition reactions have to be expected given the high thermal stress.

According to the process known from EP 2204356 A1, these difficulties are avoided by deliberately increasing the ditrimethylolpropane content in the reaction mixture. First of all, 2.0 to 3.5 mol of formaldehyde per mole of n-butyraldehyde are converted in the presence of a base. 2-Ethylacrolein formed is distilled off and added again to the trimethylolpropane-containing distillation residue together with further formaldehyde, which results in the formation of ditrimethylolpropane and formic acid. After neutralization, the mixture is freed of low boilers and worked up either by distillation or crystallization. According to EP 1178030 A2, the residue from trimethylolpropane preparation, after extraction and trimethylolpropane removal, is treated with an acid in order to split formals. Subsequently, ditrimethylolpropane is distilled off in a falling-film evaporator and purified by crystallization.

Likewise described is the direct workup of the distillation residue from trimethylolpropane preparation by recrystallization to obtain ditrimethylolpropane. DE 2358297 A1 considers the simple crystallization of an aqueous solution of the distillation residue, wherein the salt concentration in the aqueous solution is adjusted to a particular ratio in order to enable the precipitation of ditrimethylolpropane in sufficient purity. When trimethylolpropane is prepared by the Cannizzaro process, the salt content, for example the alkali metal formate content, in the distillation residue may already be sufficiently high to ensure the precipitation of ditrimethylolpropane crystals in a satisfactory manner after dissolution in water. It may be necessary to add a further salt to the aqueous solution, for example an alkali metal salt.

US 2004/0254405 A1 discloses a process for recrystallizing the distillation residue using organic solvents, for example acetone or methyl ethyl ketone, which requires a particular degree of observance of the crystallization temperature, the amount of solvent and the ditrimethylolpropane content in the distillation residue. The use of a mixture of a suitable solvent and water for the isolation of ditrimethylolpropane from the distillation residues of the trimethylolpropane preparation is described in DE 10 2008 038 021 A1. An organic solvent phase and a viscous residue are initially obtained, the phases are separated and the organic solvent phase is extracted with water. The water phase is isolated and solvent residues present are removed. Ditrimethylolpropane is crystallized from the remaining water phase.

German patent application 10 2010 033 844 A1 likewise concerns a process for obtaining ditrimethylolpropane from the secondary streams of trimethylolpropane preparation. This involves dissolving the high-boiling fractions and residues obtained in water and catalytically hydrogenating the aqueous solution in the presence of an acidic compound to split formaldehyde-containing acetals. After removal of solids, the aqueous hydrogenated material is then contacted both with basic and with acidic ion exchangers. A trimethylolpropane-enriched product stream is distilled out of the aqueous eluate, and ditrimethylolpropane remains as the distillation residue. In order that ditrimethylolpropane is obtained in sufficient quality in the distillation residue, in the process according to German patent application 10 2010 033 844 A1, the treatment of the aqueous hydrogenated material both with basic and with acidic ion exchangers is absolutely necessary.

Finally, the prior art also describes processes for the deliberate synthesis of ditrimethylolpropane. According to EP 0799815 A1 trimethylolpropane is reacted directly with 2-ethylacrolein and formaldehyde in the presence of basic catalysts. After removing volatile components, purified ditrimethylolpropane is obtained by recrystallization from water. According to WO 92/05134 A1, already isolated trimethylolpropane is heated in the presence of an acidic compound, resulting in etherification to form ditrimethylolpropane. In order to avoid the formation of higher condensation products of trimethylolpropane, not more than 30% of trimethylolpropane is converted. The volatile components are removed by distillation from the resulting reaction mixture. Ditrimethylolpropane can also first be distilled off and purified further by recrystallization. J. Org. Chem., Vol. 37, No. 13, 1972, pages 2197-2201 likewise discloses the direct preparation of ditrimethylolpropane. First of all, trimethylolpropane is converted to the ketal with acetone in order to protect two hydroxyl groups. Subsequently, the hydroxyl group still free is converted to the tosylate or mesylate group which is eliminated in the presence of bases to form ethers. Addition of acid removes the ketal protecting group and releases ditrimethylolpropane, which is recrystallized from water. This process described in the scientific literature, however, is complex and requires specialty chemicals through the introduction and detachment of protecting groups.

The known processes for obtaining ditrimethylolpropane from high-boiling fractions and residues which have a higher boiling point than trimethylolpropane and are obtained in the distillative workup in the course of trimethylolpropane preparation or in the course of the deliberate synthesis of ditrimethylolpropane require either complex recrystallization steps or a complex steam distillation with subsequent removal of water from the steam distillate. The prior art mentions the distillative removal of ditrimethylolpropane using a falling-film evaporator, but a recrystallization is recommended for further purification of the distillate.

Additionally in processes in which ditrimethylolpropane is obtained as a distillation residue, ditrimethylolpropane is not always obtained in sufficient quality to use it in a maximum number of industrial applications. In addition, prior to the distillation stage, purification with ion exchangers is necessary in order to minimize the content of impurities in the distillation residue.

There is therefore a need for a process for obtaining ditrimethylolpropane in a very simple manner and in high purity. More particularly, the content of linear bistrimethylolpropane formal (formula II) and further high-boiling compounds which exhibit boiling characteristics similar to ditrimethylolpropane is to be reduced to an acceptable limit. At the same time, complex recrystallization steps are to be avoided. The process should also be generally useable irrespective of whether ditrimethylolpropane is obtained as a by-product in the preparation of trimethylolpropane, whether the secondary streams in trimethylolpropane preparation are subjected to further process steps, such as an acid treatment, an ion exchanger treatment or a catalytic hydrogenation in the presence of an acid, or whether ditrimethylolpropane is prepared by a deliberate synthesis.

SUMMARY OF INVENTION

The present invention therefore relates to a distillative process for obtaining ditrimethylolpropane from solutions comprising ditrimethylolpropane, characterized in that:

(a) the solution comprising ditrimethylolpropane is separated in a first distillation unit into a first tops fraction comprising low-boiling compounds having a lower boiling point than ditrimethylolpropane and a bottoms fraction;

(b) the bottoms fraction obtained after step a) is introduced into a second distillation unit having at least 5 theoretical plates, said unit being configured as a thin-film evaporator with a column attachment, and a second tops fraction comprising intermediate-boiling compounds having a lower boiling point than ditrimethylolpropane is drawn off, and a bottoms fraction is withdrawn; and (c) the bottoms fraction obtained after step b) is introduced into a third distillation unit having at least 4 theoretical plates, said unit being configured as a thin-film evaporator with a column attachment, in which ditrimethylolpropane is obtained as a third tops fraction and high boilers are removed as a bottoms fraction.

BRIEF DESCRIPTION OF DRAWING

The invention is described in detail below with reference to FIG. 1 which is a schematic diagram illustrating the process and apparatus of the present invention.

DETAILED DESCRIPTION

Input streams for the distillation process according to the invention are solutions which comprise ditrimethylolpropane and are obtained independently of a particular production process. For example, these solutions are obtained in the preparation of trimethylolpropane, either by the Cannizzaro process using alkali metal or alkaline earth metal compounds or by the hydrogenation process in the presence of catalytic amounts of trialkylamines or by the Cannizzaro process using stoichiometric amounts of trialkylamines. More particularly, they are obtained in the distillative workup of trimethylolpropane as high-boiling residues. Frequently, these high-boiling residues, for splitting of the formals of the formulae I to V, are taken up in water and treated with an acid or hydrogenated in aqueous solution with hydrogen in the presence of an acidic compound and of a metal catalyst.

Solutions suitable for the distillation process according to the invention are likewise obtained in processes in which ditrimethylolpropane is prepared deliberately, for example by reaction of already isolated trimethylolpropane with 2-ethylacrolein and formaldehyde in the presence of a basic catalyst or by reaction of n-butyraldehyde and formaldehyde in the presence of a basic catalyst under such conditions that 2-ethylacrolein is first distilled out of the trimethylolpropane-containing reaction mixture and is added to the reaction mixture again together with further formaldehyde in order to convert trimethylolpropane formed in the first stage to ditrimethylolpropane. Etherification of a hydroxyl group of trimethylolpropane, optionally after introduction of a protecting group for the two other hydroxyl groups, can also give suitable solutions comprising ditrimethylolpropane.

It is likewise possible in the distillation process according to the invention to use ditrimethylolpropane which has already been purified by a prior recrystallization or has been prepurified by treatment with an ion exchanger. Examples of suitable ion exchangers for the ion exchanger treatment are customary commercially available acidic and basic ion exchangers. The solution comprising ditrimethylolpropane can be contacted either only with a basic or acidic ion exchanger, or with any combination.

The process according to the invention is particularly suitable in the distillative workup of solutions comprising ditrimethylolpropane dissolved in a polar solvent, especially in the distillative workup of aqueous solutions or solutions in a lower $C_1$-$C_5$ aliphatic alcohol or a $C_2$-$C_{10}$ dialkyl ether, such as methanol, ethanol, propanol or diethyl ether. Such alcoholic and especially aqueous solutions are obtained particularly in the acidic treatment of residues from trimethylolpropane preparation, which can additionally be effected under hydrogen in the presence of a hydrogenation catalyst.

These residues from trimethylolpropane preparation comprise, as main components still incorporated in a physical mixture, trimethylolpropane, generally in a range from 5 to 30% by weight, ditrimethylolpropane, generally in a range from 10 to 35% by weight, and linear bistrimethylolpropane formal (formula II) in a range from 25 to 70% by weight, based on the overall input composition. Further identified products are 2-ethyl-2-methyl-1,3-propanediol and the monocyclic formal of trimethylolpropane (formula I), which is present only in small amounts of typically up to 3% by weight due to its comparatively low boiling point. As well as the methyl (monolinear) formal of trimethylolpropane (formula III), the methyl (bis-linear) formal of trimethylolpropane (formula IV) and the cyclic formal of ditrimethylolpropane (formula V), or the formals of trimethylolpropane released from the methyl ethers in any upstream hydrogenation, such as:

$C_2H_5C(CH_2OH)_2CH_2OCH_2OH$     Formula VI, CAS 482619-74-9

$C_2H_5C(CH_2OH)(CH_2OCH_2OH)_2$     Formula VII

Formula VIII a series of further linear or cyclic formals of ditrimethylolpropane are also present, such as:

$C_2H_5C(CH_2OH)_2CH_2OCH_2C(C_2H_5)(CH_2OH)$
$(CH_2OCH_2OH)$     Formula IX, CAS 97416-99-4

Formula X

CAS 1252027-64-7

Formula XI
$C_2H_5 \; CH_2—O—CH_2C(C_2H_5)(CH_2OH)(CH_2OCH_2OH)$ and the monocyclic formal formed from linear bistrimethylolpropane formal (formula XII)

Formula XII
$C_2H_5C(CH_2OH)_2CH_2OCH_2OCH_2 \; C_2H_5$

These residues from trimethylolpropane preparation are admixed with a polar solvent, preferably with water, to form a solution. In general, a solution with a content of organic components, neglecting the polar solvent, of to 90% by weight and preferably of 50 to 80% by weight is prepared, based on the overall composition. Smaller contents of organic components are inappropriate due to the high solvent content; in the case of excessively high contents, particularly at room temperature, inhomogeneities in the solution or the precipitation of solids is to be expected. Appropriately, the solution is prepared at a temperature of more than 50° C. A temperature range for the solution, especially for the aqueous solution, of 60° C. to 80° C. should preferably be established.

Optionally, the resulting solution can be treated at elevated temperature and elevated pressure with hydrogen in the presence of a catalyst and of an acidic compound. The hydrogenation in an acidic medium splits the formals present and converts formaldehyde released to methanol. Optionally, the resulting solution can be contacted with an ion exchanger or with a combination of acidic and basic ion exchangers.

Irrespective of the preparation process, the solution comprising ditrimethylolpropane, in the process according to the invention, is worked up in a three-stage distillation unit. The solution comprising ditrimethylolpropane is also understood to mean a solution which comprises already purified ditrimethylolpropane, for example from a recrystallization process, in which the content of impurities having a similar boiling point to ditrimethylolpropane has already been depleted. Examples of such an impurity having a similar boiling point to ditrimethylolpropane are the linear bistrimethylolpropane formal (formula II), the monocyclic formal formed from the linear bistrimethylolpropane formal (formula XII), the monolinear formal of ditrimethylolpropane (formula IX) or the monolinear formal of the cyclic formal of ditrimethylolpropane (formula XI). Suitable solvents for already purified ditrimethylolpropane are water and lower $C_1$-$C_5$ aliphatic alcohols such as methanol, ethanol or propanol. Already isolated, solid ditrimethylolpropane, after melting, is also regarded as a solution comprising ditrimethylolpropane in the context of the present invention.

The solution comprising ditrimethylolpropane is worked up in a three-stage distillation unit. First of all, in a first distillation unit, low boilers are removed as the first tops fraction. Suitable distillation units for the low boiler removal are those which are customary, such as a distillation column having, for example, 2 to 40 theoretical plates, with a boiler, a thin-film evaporator, a short-path evaporator or a vaporization vessel, which is typically operated at bottom temperatures of 100 to 180° C. and at standard pressure or appropriately under reduced pressure down to 70 hPa. The feed to the first distillation unit can be introduced at room temperature, but the feed advantageously has a temperature of 50 to 130° C., especially 80 to 120° C. An elevated temperature is required when a ditrimethylolpropane melt is introduced. The introduction of the feed already at an elevated temperature can cause low boilers to be removed to evaporate instantly and be removed via the first tops fraction.

If a solution of ditrimethylolpropane in a polar solvent is used, the first distillation unit serves to remove the polar solvent and further low boilers, for example methanol, 2-methylbutanol, 2-ethyl-2-methyl-1,3-propanediol or volatile formals. The first distillation unit is operated such that the content of the polar solvent in the bottoms fraction comprising ditrimethylolpropane is not more than 5000 ppm by weight, preferably up to 1000 ppm by weight and especially up to 500 ppm by weight, based on the mass of the bottoms fraction. Complying with a maximum limit for the solvent content in the bottoms fraction has an advantageous effect on the subsequent distillative purification. A suitable polar solvent is a lower $C_1$-$C_5$ aliphatic alcohol or $C_2$-$C_{10}$ dialkyl ether, such as methanol, ethanol, propanol or diethyl ether, or especially water.

This bottoms fraction from the first distillation unit is removed and introduced to a second distillation unit.

In the second distillation unit, the second tops fraction obtained is an intermediate-boiling product stream in which compounds having a higher boiling point than the low boilers removed in the first tops fraction but a lower boiling point than ditrimethylolpropane are present. If a mixture comprising trimethylolpropane and ditrimethylolpropane is worked up, the second tops fraction comprises essentially trimethylolpropane and additionally also intermediate fractions and residues of the polar solvent and of low boilers. The intermediate-boiling tops fraction also comprises, for example, the monolinear formal of trimethylolpropane (formula VI), the bis-linear formal of trimethylolpropane (formula VII), the monolinear formal of the cyclic formal of trimethylolpropane (formula VIII), and also the monocyclic formal of ditrimethylolpropane (formula V) and the bis-cyclic formal of ditrimethylolpropane (formula X). These oxygen containing compounds can also be embraced by the intermediate fraction I. The second tops fraction can then appropriately be recycled into the purification stage of the overall process for the preparation of trimethylolpropane, advantageously into the purifying distillation to obtain trimethylolpropane.

The second tops fraction is removed in a distillation unit having at least 5 theoretical plates, preferably at least 8 theoretical plates and especially 8 to 20 theoretical plates. The thermal stress in the second distillation unit should likewise be kept at a minimum, and minimum residence times should be employed. The residence time in the second distillation unit, i.e. in the overall distillation apparatus, is generally from 2 to 60 and preferably from 10 to 30 seconds. The plant connection used is a thin-film evaporator with a column attachment having the required minimum number of theoretical plates. Suitable column attachments are conventional columns with random packing or structured packing, preferably columns with structured packing. Such structured packings are commercially available, for example in the form of Montz or Sulzer packings. The thin-film evaporators for use in the process according to the invention are units customary in the art, which are commercially available. Unsuitable are a boiler with column attachment or short-path evaporator, since, in this arrangement, either the residence time in the distillation unit is too high or the separation performance is inadequate. The second distillation unit is operated generally at bottom temperatures of 210 to 280° C. and at a pressure of 2 to 10 hPa. The bottoms fraction from the second distillation unit is subsequently introduced into a third distillation unit.

The third distillation unit can also be regarded as a tailings removal unit and serves to obtain ditrimethylolpropane in sufficient quality. Ditrimethylolpropane is removed as the third tops fraction, and high boilers are removed as the bottoms fraction from the third distillation unit. The high boilers comprise, for example, the monocyclic formal of linear bistrimethylolpropane formal (formula XII) and the cyclic formal of ditrimethylolpropane (formula XI), and also the monolinear formal of ditrimethylolpropane (formula IX). These oxygen containing compounds can also be embraced by the intermediate fraction II. In order to obtain ditrimethylolpropane in sufficient quality, the third distillation unit has to have at least 4 theoretical plates and especially 4 to 20 theoretical plates. In the third distillation column too, the thermal stress should likewise be kept at a minimum, and minimum residence times should be employed. The residence time of the tops fraction in the third distillation unit is generally from 1 to 30 and preferably from 5 to 20 seconds. The plant connection used is a thin-film evaporator with a column attachment having the required minimum number of theoretical plates. Suitable column attachments are conventional columns with random packing or structured packing, preferably columns with structured packing. Such structured packings are commercially available, for example as Montz or Sulzer packings. The thin-film evaporators for use in the process according to the invention are also units customary in the art, which are commercially available. Unsuitable are a boiler with a column attachment or a short-path evaporator, since, in this arrangement, either the residence time of the top product in the distillation unit is too high or the separation performance is inadequate. The third distillation unit is operated generally at bottom temperatures of 240 to 280° C. and at a pressure of 0.2 to 5 hPa. A maximum bottom temperature of 280° C. should not be exceeded in order to avoid excessive decomposition of ditrimethylolpropane.

The ditrimethylolpropane removed via the tops fraction is obtained in a quality sufficient for industrial applications, and it is possible to obtain product of value contents determined by gas chromatography of greater than 98% by weight. The distillation process according to the invention can effectively remove high-boiling impurities having a comparably high boiling point to ditrimethylolpropane, for example linear bistrimethylolpropane formal (formula II) or compounds having boiling points higher than trimethylolpropane but comparable to ditrimethylolpropane, such as the compounds embraced by intermediate fraction I. It is also possible to achieve sulphate ash contents, determined to DIN 51575, modified by addition of sulphuric acid after the burning and before the annealing of the sample, in the distillatively purified ditrimethylolpropane of less than 100 ppm and generally between 15 and 80 ppm.

Figure 1:
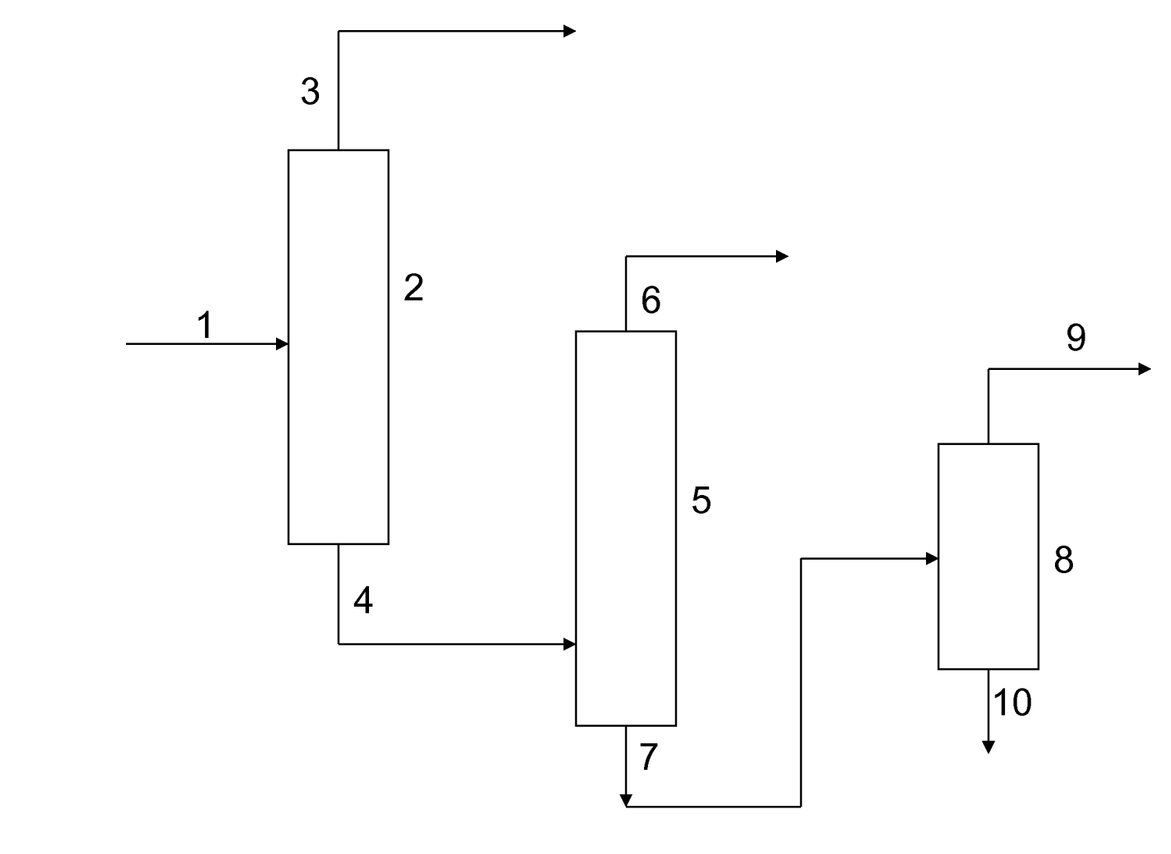

FIG. 1 shows a block diagram for the distillative treatment of the solution comprising ditrimethylolpropane. The preferably heated solution introduced via line (1) is fed to a first distillation unit (2) in which the first tops fraction comprising the polar solvent and low boilers, for example water or methanol, is removed at the top via line (3). Via the bottom of the first distillation unit (2), the bottoms fraction is removed with line (4). The first distillation unit is a customary column with, for example, 2 to 40 theoretical plates. If an aqueous or alcoholic solution is being worked up, the first distillation unit is operated such that the water or alcohol content in the bottoms fraction removed via line (4) is not more than 5000 ppm by weight based on the mass of the bottoms fraction. The bottoms fraction from the first distillation unit (2) is fed to a second distillation unit (5) which has at least 5 theoretical plates and which is configured as a thin-film evaporator with a column attachment. Via line (6), the second tops fraction is withdrawn, which comprises, for example, trimethylolpropane, intermediate fractions such as the intermediate-boiling compounds embraced by intermediate fraction I, and residues of the polar solvent and of low boilers. If the trimethylolpropane content in the second tops fraction is sufficiently high, this product stream can appropriately be recycled into the process for preparing trimethylolpropane. The bottoms fraction from the second distillation unit (5) is removed via line (7) and fed to the third distillation unit (8). This third distillation unit or else tailings removal unit has at least 4, for example 5, theoretical plates and is configured as a thin-film evaporator with column attachment. Via line (9), ditrimethylolpropane is removed as the tops fraction in high quality, while high boilers are discharged via line (10) from the process.

The process according to the invention permits the distillative workup of solutions comprising ditrimethylolpropane and the effective removal of high-boiling impurities having boiling points comparable to ditrimethylolpropane, such as the compounds embraced by intermediate fractions I and II. Ditrimethylolpropane can generally be obtained with a high product of value content of greater than 98% by weight, determined by gas chromatography. It is also possible to achieve sulphate ash contents, determined to DIN 51575, modified, of less than 100 ppm.

If the solutions comprising ditrimethylolpropane used in the process according to the invention are the residues from trimethylolpropane preparation, it is simultaneously possible to remove trimethylolpropane-enriched product streams and recycle them into the preparation process for trimethylolpropane, such that the plant efficiency and the trimethylolpropane yield can also be improved overall.

The examples which follow describe the process according to the invention in detail. It is of course not restricted to the embodiment described.

Example 1

For the distillative workup, an aqueous solution which contained 40% by weight of water and 60% by weight of organic components was used, and the organic fraction had the following composition (%) determined by gas chromatography:

| | |
|---|---|
| Forerun | 6.3 |
| Monocyclic formal (I) | 0.3 |
| Trimethylolpropane | 64.4 |
| Intermediate fraction I | 0.6 |
| Ditrimethylolpropane | 28.0 |
| Intermediate fraction II | 0.1 |
| Linear bistrimethylolpropane formal (II) | 0.1 |
| High boilers | 0.2 |

Example 1a(1): Removal of Water and Forerun

In a first distillation, in a 20-tray column with a boiler at a bottom temperature of 96° C. and at a pressure of 73 mbar hPa, water and low boilers were removed as distillate. The resulting distillation bottoms contained about 800 ppm by weight of water and had the following composition (%) determined by gas chromatography:

| | |
|---|---|
| Forerun | 0.6 |
| Monocyclic formal (I) | 0.1 |
| Trimethylolpropane | 72.0 |
| Intermediate fraction I | 0.8 |
| Ditrimethylolpropane | 26.0 |
| Intermediate fraction II | 0.1 |
| Linear bistrimethylolpropane formal (II) | 0.1 |
| High boilers | 0.3 |

Example 1a(2): Low Boiler Removal, Trimethylolpropane Depletion

The bottom product according to Example 1a(1) was subjected to another distillation in a 20-tray column with a boiler. The pressure applied was 3 hPa at a bottom temperature of 255° C. A reflux ratio of 1:1 was established. The resulting bottom product had the following composition (%) determined by gas chromatography:

| | |
|---|---|
| Forerun | 0.1 |
| Monocyclic formal (I) | 0.0 |
| Trimethylolpropane | 2.4 |
| Intermediate fraction I | 1.6 |
| Ditrimethylolpropane | 93.4 |
| Intermediate fraction II | 0.8 |
| Linear bistrimethylolpropane formal (II) | 0.0 |
| High boilers | 1.7 |

Example 1b: Removal of Trimethylolpropane-Enriched Product Streams

The bottom product from the first distillation according to Example 1a(1) (70/30 mixture) was used for the second distillation. The second distillation was configured such that intermediate fractions I and II, which have a boiling point comparable to ditrimethylolpropane, were depleted as far as possible in the distillation bottoms. Table 1 compiles different embodiments for the second distillation. The gas chromatography analysis shows the composition (%) of the input and the composition of the distillation bottoms.

TABLE 1

Removal of trimethylolpropane-enriched product streams from the
distillation bottoms according to Example 1a(1) [input: 70/30
mixture]; gas chromatography analysis of the bottom products

|  |  | Input (70/30 mixture) | 1b (1) Thin-film evaporator with column having random packing | 1b (2) Thin-film evaporator with column having structured packing | 1b (3) comparative Only column with structured packing and a boiler |
|---|---|---|---|---|---|
| Temperatures | | | | | |
| Top | [° C.] | | 160 | 163 | 165 |
| Side | [° C.] | | — | 242 | 190 |
| Casing/bottom | [° C.] | | 270 | 265 | 269 |
| Column top | [hPa] | | 5 | 5 | 4 |
| Pressure differential | [hPa] | | 29 | 11 | 17 |
| Reflux ratio | | | 1/3 | none | none |
| Top draw | [%] | | 76 | 75.3 | 77 |
| Bottom draw | [%] | | 24 | 24.7 | 23 |
| Number of plates | | | 11 | 15 | 15 |
| Residence time | [s] | | 10-30 | 10-30 | 3-5 hours |
| Gas chromatography composition (%): | | | | | |
| Forerun | | 0.6 | 0.1 | 0.1 | 0.1 |
| Monocyclic formal (I) | | 0.1 | 0.0 | 0.0 | 0.0 |
| Trimethylolpropane | | 72.0 | 0.1 | 0.3 | 0.1 |
| Intermediate fraction I | | 0.8 | 1.5 | 0.4 | 0.9 |
| Ditrimethylolpropane | | 26.0 | 97.3 | 98.1 | 97.5 |
| Intermediate fraction II | | 0.1 | 0.1 | 0.1 | 0.1 |
| Linear bistrimethylol-propane formal (II) | | 0.1 | 0.1 | 0.0 | 0.1 |
| High boilers | | 0.3 | 0.8 | 1.0 | 1.2 |

As Example 1b(2) shows, the use of a column with structured packing, for example a column having a diameter of 40 mm equipped with a Montz packing, allows depletion of the intermediate fraction I in the bottoms. In Example 1b(3), comparatively long residence times have to be employed such that, at the high distillation temperatures, decomposition occurs to form volatile compounds and a comparatively high pressure differential is observed during the distillation compared to Example 1b(2), which works with the same column type. Nevertheless, in this configuration of the second distillation too, a bottom product with a ditrimethylolpropane content of 97.5% is obtained.

The use of a column with structured packing and a higher number of separation stages is, however, preferable over a column with random packing.

For the subsequent distillation experiments 1b(4)-1b(6), the bottom product from the low boiler removal and trimethylolpropane depletion according to Example 1a(2) (93% material) was used. The conditions of the second distillation and the gas chromatography analysis of the bottom product (%) are compiled in Table 2 below.

TABLE 2

Removal of trimethylolpropane-enriched product streams from
the bottom product according to Example 1a(2) (93% material,
input), gas chromatography analysis of the bottom products

|  |  | Input (93% material) | 1b (4) Thin-film evaporator with column with structured packing | 1b (5) comparative Only column with random packing and boiler | 1b (6) comparative Only short-path evaporator with no column |
|---|---|---|---|---|---|
| Temperatures | | | | | |
| Top | [° C.] | | 145-175 | 144-215 | 185-190 |
| Side | [° C.] | | 149-180 | 148-223 | — |
| Casing/bottom | [° C.] | | 260 | 270 | 200 |
| Column top | [hPa] | | 1-2 | 4 | 3 |
| Pressure differential | [hPa] | | 8 | 16 | — |
| Reflux ratio | | | ½ | 2/1 | none |
| Top draw | [%] | | 24.3 | 13.1 | 50 |
| Bottom draw | [%] | | 75.7 | 86.9 | 50 |
| Number of plates | | | 5 | 15 | 1 |
| Residence time | [s] | | 10-30 | 3-5 hours | 5-20 |
| Gas chromatography composition (%): | | | | | |
| Forerun | | 0.1 | 0.1 | 0.1 | 0.0 |
| Monocyclic formal (I) | | 0.0 | 0.0 | 0.0 | 0.0 |

TABLE 2-continued

Removal of trimethylolpropane-enriched product streams from
the bottom product according to Example 1a(2) (93% material,
input), gas chromatography analysis of the bottom products

|  | Input (93% material) | 1b (4) Thin-film evaporator with column with structured packing | 1b (5) comparative Only column with random packing and boiler | 1b (6) comparative Only short-path evaporator with no column |
|---|---|---|---|---|
| Trimethylolpropane | 2.4 | 0.3 | 0.1 | 2.3 |
| Intermediate fraction I | 1.6 | 0.7 | 0.7 | 2.3 |
| Ditrimethylolpropane | 93.4 | 97.7 | 96.7 | 94.1 |
| Intermediate fraction II | 0.8 | 0.1 | 0.1 | 0.2 |
| Linear bistrimethylol-propane formal (II) | 0.0 | 0.0 | 0.0 | 0.0 |
| High boilers | 1.7 | 1.1 | 2.3 | 1.1 |

As Comparative Example 1b(6) shows, it is not possible to deplete the intermediate fraction I in the bottom product of the second distillation when working without a column attachment and only with a short-path evaporator. For the depletion of intermediate fraction I, according to Example 1b(4), a column attachment with theoretical plates is needed, even if the distillation input already has a high content of ditrimethylolpropane.

Example 1c: Tailings Removal

The bottom product obtained according to Example 1b(3) was used for the third distillation for tailings removal. The desired ditrimethylolpropane was obtained as the top product in sufficient quality. The distillation conditions and the gas chromatography analysis (%) of the distillate are reported in Table 3.

As the comparison of Examples 1c(7) and 1c(9) with Comparative Example 1c(8) shows, the use of a thin-film evaporator with a column attachment is required to obtain ditrimethylolpropane as the top product in sufficient quality. A distillation unit composed of boiler with column attachment is unsuitable for tailings removal since, in the case of this arrangement, the high temperatures and long residence times cause increased decomposition, indicated by distinct formation of forerun and decrease in the ditrimethylolpropane content.

The invention claimed is:

1. Distillative process for obtaining ditrimethylolpropane from solutions comprising ditrimethylolpropane, consisting of:
   (a) separating the solution comprising ditrimethylolpropane in a first distillation unit into a first tops fraction

TABLE 3

Tailings removal from the bottom product according to Example
1b(3), gas chromatography analysis (%) of the distillate

|  |  | Input Example 1b(3) | 1c (7) Thin-film evaporator with column with structured packing | 1c (8) comparative Only column with random packing and boiler | 1c (9) Thin-film evaporator with column with structured packing |
|---|---|---|---|---|---|
| Temperatures | | | | | |
| Top | [° C.] |  | 222 | 235 | 155 |
| Side | [° C.] |  | 230 | 240 | 160 |
| Bottom | [° C.] |  | 265 | 290-70 | 265 |
| Column top | [hPa] |  | 3 | 5 | 0.3 |
| Pressure differential | [hPa] |  | 10 | 30-35 | — |
| Reflux ratio |  |  | none | none | none |
| Top draw | [%] |  | 90.1 | 76.2 | 95.4 |
| Bottom draw | [%] |  | 9.9 | 23.8 | 4.6 |
| Number of plates |  |  | 15 | 15 | 15 |
| Residence time | [s] |  | 5-8 | 3-5 hours | 5-9 |
| Gas chromatography composition (%): | | | | | |
| Forerun |  | 0.1 | 0.0 | 11.5 | 0.0 |
| Monocyclic formal (I) |  | 0.0 | 0.0 | 0.0 | 0.0 |
| Trimethylolpropane |  | 0.1 | 0.6 | 14.8 | 0.5 |
| Intermediate fraction I |  | 0.9 | 0.1 | 2.2 | 0.1 |
| Ditrimethylolpropane |  | 97.5 | 98.6 | 70.7 | 98.5 |
| Intermediate fraction II |  | 0.1 | 0.5 | 0.3 | 0.7 |
| Linear bistrimethylol-propane formal (II) |  | 0.1 | 0.0 | 0.1 | 0.1 |
| High boilers |  | 1.2 | 0.2 | 0.4 | 0.1 |
| Ash value DIN 51575 modified |  |  | <50 ppm | — | <50 ppm |
| Gardner colour number ASTM D1544 |  | >6 | 1 | 1 | 1 | comprising low-boiling compounds having a lower boiling point than ditrimethylolpropane and a bottoms fraction;

(b) introducing the bottoms fraction as obtained after step a) into a second distillation unit having at least 5 theoretical plates, said unit being configured as a thin-film evaporator with a column attachment, and drawing off a second tops fraction comprising intermediate-boiling compounds having a lower boiling point than ditrimethylolpropane, and withdrawing a bottoms fraction; and (c) introducing the bottoms fraction as obtained after step b) into a third distillation unit having at least 4 theoretical plates, said unit being configured as a thin-film evaporator with a column, attachment, in which ditrimethylolpropane is obtained as a third tops fraction and high boilers are removed as a bottoms fraction.

2. Process according to claim 1, characterized in that the second distillation unit has at least 8 theoretical plates.

3. Process according to claim 1, characterized in that, in step b) the column attachment is configured as a column with random packing or column with structured packing.

4. Process according to claim 1, characterized in that the second distillation unit is operated at a temperature of 210 to 280° C. and at a pressure of 2 to 10 hPa.

5. Process according to claim 1, characterized in that the second distillation unit is operated with a residence time of 2 to 60 seconds.

6. Process according to claim 1, characterized in that the third distillation unit has 4 to 20 theoretical plates.

7. Process according to claim 1, characterized in that, in step c) the column attachment is configured as a column with random packing or column with structured packing.

8. Process according to claim 1, characterized in that the third distillation unit is operated at a temperature of 240 to 280° C. and at a pressure of 0.2 to 5 hPa.

9. Process according to claim 1, characterized in that the residence time of the tops fraction in the third distillation unit is 1 to 30 seconds.

10. Process according to claim 1, characterized in that a solution of ditrimethylolpropane in a polar solvent is separated in the first distillation unit.

11. Process according to claim 10, characterized in that the content of the polar solvent in the bottoms fraction of the first distillation unit is up to 5000 ppm by weight, based on the bottoms fraction.

12. Process according to claim 11, characterized in that the content of the polar solvent in the bottoms fraction of the first distillation unit is up to 1000 ppm by weight, based on the bottoms fraction.

13. Process according to claim 10, characterized in that the polar solvent used is a $C_1$-$C_5$ aliphatic alcohol, a $C_2$-$C_{10}$ dialkyl ether or water.

14. Process according to claim 3, characterized in that the second distillation unit is operated at a temperature of 210 to 280° C. and at a pressure of 2 to 10 hPa.

15. Process according to claim 3, characterized in that the second distillation unit is operated with a residence time of 2 to 60 seconds.

16. Process according to claim 7, characterized in that the third distillation unit is operated at a temperature of 240 to 280° C. and at a pressure of 0.2 to 5 hPa.

17. Process according to claim 7, characterized in that the residence time of the tops fraction in the third distillation unit is 1 to 30 seconds.

18. Distillative process for obtaining ditrimethylolpropane from solutions comprising ditrimethylolpropane, consisting of:

(a) producing the solution comprising ditrimethylolpropane from the residues of trimethyl propane with the addition of water and separating the comprising ditrimethylolpropane in a first distillation unit into a first tops fraction comprising low-boiling compounds having a lower boiling point than ditrimethylolpropane and a bottoms fraction;

(b) introducing the bottoms fraction as obtained after step a) into a second distillation unit having at least 5 theoretical plates, said unit being configured as a thin-film evaporator with a column attachment, and drawing off a second tops fraction comprising intermediate-boiling compounds having a lower boiling point than ditrimethylolpropane is, and withdrawing a bottoms fraction; and (c) introducing the bottoms fraction as obtained after step b) into a third distillation unit having at least 4 theoretical plates, said unit being configured as a thin-film evaporator with a column attachment, in which ditrimethylolpropane is obtained as a third tops fraction and high boilers are removed as a bottoms fraction.

19. Distillative process for obtaining ditrimethylolpropane from solutions comprising ditrimethylolpropane, consisting of:

(a) treating the solution comprising ditrimethylolpropane with an ion exchanger and separating the solution comprising ditrimethylolpropane in a first distillation unit into a first tops fraction comprising low-boiling compounds having a lower boiling point than ditrimethylolpropane and a bottoms fraction;

(b) introducing the bottoms fraction as obtained after step a) into a second distillation unit having at least 5 theoretical plates, said unit being configured as a thin-film evaporator with a column attachment, and drawing off a second tops fraction comprising intermediate-boiling compounds having a lower boiling point than ditrimethylolpropane, and withdrawing a bottoms fraction; and (c) introducing the bottoms fraction as obtained after step b) into a third distillation unit having at least 4 theoretical plates, said unit being configured as a thin-film evaporator with a column, attachment, in which ditrimethylolpropane is obtained as a third tops fraction and high boilers are removed as a bottoms fraction.

20. Process according to claim 19, characterized in that the ion exchanger treatment is effected both with a basic and with an acidic ion exchanger in any sequence.

* * * * *